Feb. 14, 1950 T. J. MORRIS Plant Pat. 922
ROSE PLANT
Filed Aug. 30, 1948
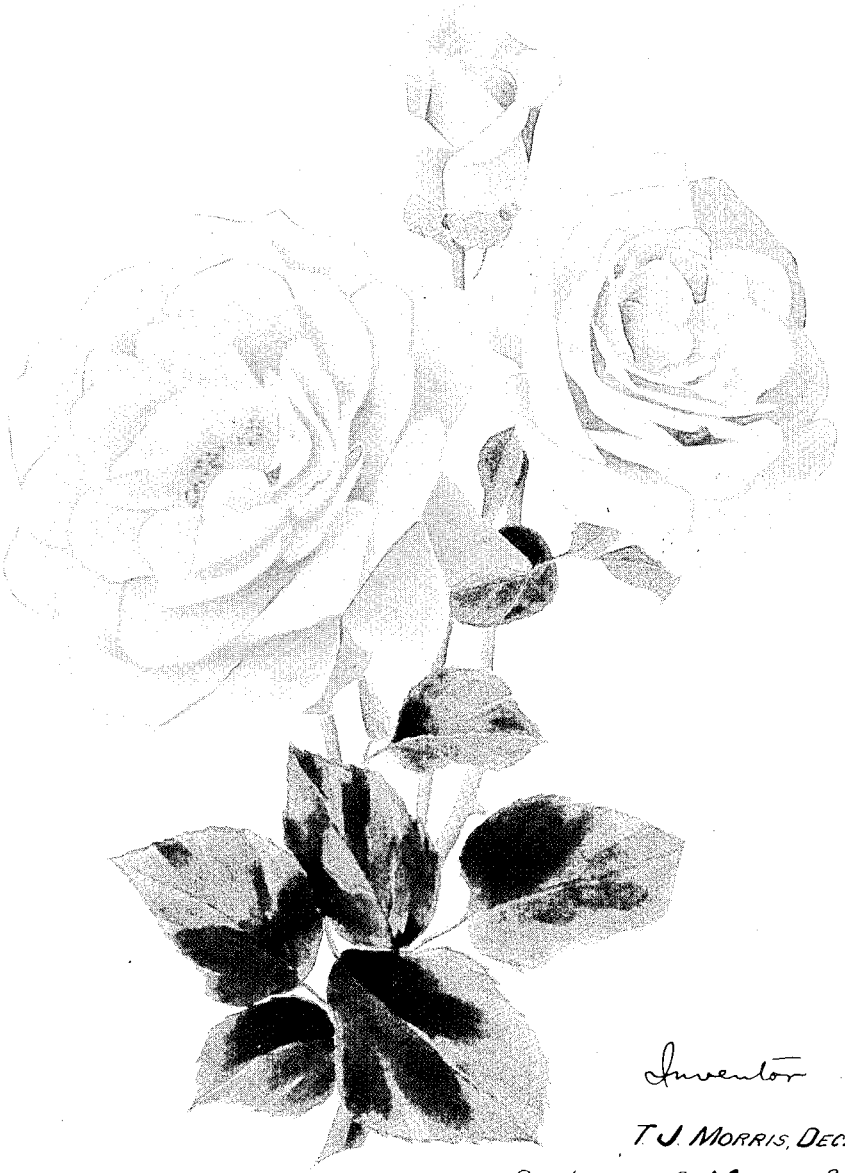
Inventor
T. J. MORRIS, DECEASED
BY LILLIAN A. MORRIS, AD'TRIX.
By Robb & Robb
Attorneys Patented Feb. 14, 1950

Plant Pat. 922

UNITED STATES PATENT OFFICE

922

ROSE PLANT

Theodore John Morris, deceased, late of Van Nuys, Calif., by Lillian Adelle Morris, administratrix, Van Nuys, Calif., assignor to Germain's Inc., Van Nuys, Calif., a corporation of California Application August 30, 1948, Serial No. 46,861

1 Claim. (Cl. 47—61)

The present invention relates to a new and distinct variety of rose plant resulting from crossing two unnamed seedlings with the objective of improving these parent varieties with respect to the color of the flowers and other plant characteristics. These objectives have been accomplished as will appear more fully hereinafter.

This new variety is characterized by the exceptionally bright and unfading color of its blossoms, its long, strong stems adapting it particularly for use for cut-flower and garden decoration purposes, its heavy foliage, the long keeping qualities of the bloom both on the plant and as a cut flower, and the habit of said flower of opening slowly in all types of weather.

The variety of rose most like this new variety is "Texas Centennial" (Pl. Pat. No. 162), the primary distinctions therefrom residing in the heavier foliage and the Bright China Rose shade color of the blooms.

Asexual reproduction of this new variety shows the foregoing characteristics come true to form and are established.

In the drawings are shown specimens of this new rose at different states of development of the flowers.

The following is a detailed description of the new variety, color terminology being in accordance with the Royal Horticultural Society Color Chart, except where otherwise indicated to have ordinary dictionary significance:

Type: Half hardy; bush; outdoor; seedling; for cut flowers and garden decoration.
Class: Hybrid tea.
Breeding: Seedling.
*Seed parent.*—Unnamed seedling.
*Pollen parent.*—Unnamed seedling.
Propagation: Holds its distinguishing characteristics through succeeding propagations by cuttings, grafting and budding.

*Flower*

Locality where grown: Van Nuys, California.
Flowers borne: Singly to stem; on strong, long stems.
Quantity of bloom: Free; outdoors.
Continuity: Continuous.
Fragrance: Moderate; sweetbrier.

Bud:
*Peduncle.*—Medium length; heavy; stiff; reddish; almost smooth; few red hairs.
*Before calyx breaks.*—Size—medium. Form—ovoid; without foliaceous appendages on the surface of the bud; with slender foliaceous parts extending beyond the tip of the bud equal to ¼ of its length. Color—Green with red suffusions.
*As calyx breaks.*—Color—China Rose, Plate o24/1.
*As first petal opens.*—Size—medium. Form—globular. Color—outside: Tyrian Rose, Plate 24/2; inside: China Rose, Plate o24/1.
*Opening.*—Opens up well; retarded by cold weather.
Bloom: Size, when fully open, large; 5″ to 6″.
*Petalage.*—Double; from 32 to 35 petals arranged regularly.
*Form.*—Cupped; becoming flat; petals remaining at first loosely flat, rolled outward; becoming later, at maturity, loosely rolled outward.
Petals: Thick; soft; with inside and outside satiny.
*Shape.*—Outside—obovate. Intermediate—obovate. Inside—scalloped irregular with one notch.

This description of a newly opened flower was made from a rose grown outdoors in the month of June, at Van Nuys, California:

*Color.*—*Outside petal*—outside surface—Tyrian Rose, Plate 24/2; inside surface—China Rose, Plate o24/1. *Intermediate petal*—outside surface—Tyrian Rose, Plate 24/2; inside surface—China Rose, Plate o24/1. *Inner petal*—outside surface—Tyrian Rose, Plate 24/2; inside surface—China Rose, Plate o24/1.

This description was made from a rose that was open for three days outdoors in the month of June at Van Nuys, California:

*Color.*—*Outside petal*—outside surface—Tyrian Rose, Plate 24/2; inside surface—China Rose, Plate o24/1. *Inside petal*—outside surface—Tyrian Rose, Plate 24/2; inside surface—China Rose, Plate o24/1.

*General color effect.*—Newly opened flower —China Rose, Plate o24/1. Three days open—China Rose, Plate o24/1.

*Behavior.*—Drop off cleanly; opens very slowly in all types of weather.

*Flower longevity.*—On bush in garden—5 days. Cut roses grown outdoors, kept at living room temperatures—6 days.

*Reproductive organs*

Stamens: Many; arranged regularly about pistils.

Filaments: Long; many; most with anthers. Color—Pink.

Anthers: Medium size; all open at once. Color —Yellow.

Pollen: Moderate yellow.

Pistils: Medium number.

Styles: Even; medium length; thin; bunched.

Stigma: White.

Ovaries: Some protruding from calyx.

Hips: Flat; with inconspicuous neck; green grey; smooth; thin.

Sepals: Permanent; long; recurved. Color—Green with red suffusion.

Seeds: Very few; medium size.

*Plant*

Foliage:

*Leaves.*—Compound of five leaflets; normal quantity; large; heavy.

*Leaflets.*—Shape, mucronate; base round; margin irregularly serrate.

*Color.* — *Mature* — upper surface — dark green; under surface—grey green. *Young* —upper surface—moderately green bronze; under surface—light bronze.

*Rachis.*—Medium heavy. Upper side—grooved; under side—extremely smooth.

*Stipules.*—Medium long; medium wide; with medium long points, turning out at an angle of less than 90°.

*Disease.*—Subject to mildew.

Growth:

*Habit.*—Upright; little branched.

*Growth.*—Vigorous.

*Canes.*—Heavy.

*Main stems.*—Dull green. *Thorns*—several; medium length; straight; with broad base. *Prickles and hairs*—none.

*Branches.*—Dull green. *Thorns*—several; medium length; hooked downward; with long narrow base. *Prickles and hairs*—none.

*New shoots.*—Dull bronze. *Thorns*—several; medium length; hooked downward; with long narrow base. *Prickles and hairs*—none.

It is claimed:

A new and distinct variety of rose plant characterized as to novelty by the exceptionally bright unfading color of its blooms; their long keeping qualities both on the plant and as cut-flowers; their habit of opening slowly in all types of weather; its heavy foliage and long, strong stems bearing single blooms, substantially as shown and described.

LILLIAN ADELLE MORRIS,
*Administratrix of the Estate of Theodore John Morris, Deceased.*

No references cited.